(12) United States Patent
Matsuda et al.

(10) Patent No.: US 6,383,518 B1
(45) Date of Patent: May 7, 2002

(54) PHOSPHATE-BINDING POLYMER PREPARATIONS

(75) Inventors: Katsuya Matsuda; Ryuji Kubota, both of Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/381,506

(22) PCT Filed: Apr. 3, 1998

(86) PCT No.: PCT/JP98/01536

§ 371 Date: Sep. 21, 1999

§ 102(e) Date: Sep. 21, 1999

(87) PCT Pub. No.: WO98/44933

PCT Pub. Date: Oct. 15, 1998

(30) Foreign Application Priority Data

Apr. 4, 1997 (JP) ............................................. 9-086581

(51) Int. Cl.[7] .............................. A61K 9/20; A61K 9/28
(52) U.S. Cl. ........................ 424/464; 424/465; 424/474; 514/781; 514/783
(58) Field of Search .................. 424/464, 465, 424/474, 480, 482

(56) References Cited

U.S. PATENT DOCUMENTS

| | | |
|---|---|---|
| 4,605,701 A | 8/1986 | Harada et al. |
| 4,631,305 A | 12/1986 | Guyer et al. |
| 5,456,920 A | 10/1995 | Matoba et al. |
| 5,496,545 A | 3/1996 | Holmes-Farley et al. |
| 5,667,775 A * | 9/1997 | Holmes-Farley et al. 424/78.11 |

FOREIGN PATENT DOCUMENTS

| | | |
|---|---|---|
| EP | 488139 | 6/1992 |
| JP | 63-253027 | 10/1988 |
| JP | 2-286621 | 11/1990 |
| JP | 4-13627 | 1/1992 |
| JP | 5-246861 A | 9/1993 |
| JP | 6-157325 | 6/1994 |
| JP | 8-198761 | 8/1996 |
| WO | 9621454 | 7/1996 |
| WO | 9639156 | 12/1996 |
| WO | WO97-04789 | 2/1997 |

OTHER PUBLICATIONS

JP 5–246861 (publication date Sep. 24, 1993); and EP 0488139 (publication date Jun. 3, 1992); Hokuriku Seiyaku Co., Ltd. (Abstract only of EP '139).

JP 4–13627 (publication date Jan. 17, 1992); Mitsubishi Kasei Corp. Abstract only.

JP 2–286621 (publication date Nov. 26, 1990); Mitsubishi Kasei Corp.; Abstract only.

(List continued on next page.)

*Primary Examiner*—James M. Spear
(74) *Attorney, Agent, or Firm*—Browdy and Neimark, P.L.L.C.

(57) ABSTRACT

A tablet containing a phosphate-binding polymer, which has an average particle size of 400 µm or less, contains particles of 500 µm or less in particle size at a ratio of 90% or more and has a moisture content of 1 to 14%, together with crystalline cellulose and/or low substituted hydroxypropylcellulose, and a process for producing the same are disclosed. The phosphate-binding polymer tablet according to the present invention contains the active component at a high ratio, is excellent in the ability to bind to phosphate and is a quickly disintegrated in an acidic to a neutral region while being little affected by the stirring strength. Accordingly, it is an excellent preparation capable of regulating changes in bioavailability due to the gastrointestinal motions and pH value.

20 Claims, 6 Drawing Sheets

Relationship between moisture content of phosphate-binding polymer and tablet hardness —○— 300 mg of phosphate-binding polymer
---△--- 200 mg of phosphate-binding polymer + 100 mg of crystalline cellulose

OTHER PUBLICATIONS

JP 8–198761 (publication date Aug. 6, 1996); Hokuriko Seiyaku Co., Ltd.; Abstract only.

WO 97–04789 (publication date Feb. 13, 1997) and EP 0878198 (publication date Nov. 18, 1998); Hisamitsu Pharmaceutical Co., Inc.; Abstract only of EP '198.

JP 6–157325 (publication date Jun. 3, 1994); Mitsubishi Kasei Corp.; Abstract only.

JP 63–253027 (publication date Oct. 20, 1988); and EP 273209 (publication date Jul. 6, 1988); American Cyanamid Co., U.S.; Abstract only of EP '209.

* cited by examiner

PHOSPHATE-BINDING POLYMER PREPARATIONS

CROSS REFERENCE TO RELATED APPLICATION

The present application is the national stage under 35 U.S.C. 371 of PCT/JP98/01536, filed Apr. 3, 1998.

TECHNICAL FIELD

This invention relates to a tablet containing a phosphate-binding polymer. More particularly, it relates to the tablet containing a phosphate-binding polymer, which has an average particle size of 400 μm or less, contains particles of 500 μm or less in particle size at a ratio of 90% or more and has a moisture content of 1 to 14%, together with crystalline cellulose and/or low substituted hydroxypropylcellulose, and showing a rapid disintegration, dispersibility and an ability to bind to phosphate, and a process f or producing the same.

BACKGROUND ART

Phosphate-binding polymers, which are non-absorptive polymers capable of adsorbing phosphate, are useful as remedies for hyperphosphatemia induced by renal hypofunction such as renal insufficiency. As described in, for example, U.S. Pat. No. 5,496,545, phosphate-binding polymers are publicly known as cationic polymer compounds comprising primary and secondary amines which are prepared by crosslinking polyallyamine with the use of a crosslinking agent such as epichlorohydrin.

With respect to phosphate-binding polymer preparations as remedies for hyperphosphatemia, for example, U.S. Pat. No. 5,496,545 points out that tablets can be produced by using various additives including crystalline cellulose. However, the patent cited above presents no particular example of such preparations. Although the present inventors attempted in practice to produce tablets by blending various additives with the phosphate-binding polymer obtained by the method as described in the above patent, no tablet could be successfully produced thereby.

Moreover, known adsorbents for oral administration, for example, a calcium polystyrene sulfonate preparation (Kalimate™ manufactured by Nikken Chemicals Co., Ltd.), a sodium polystyrene sulfonate preparation (Kayexalate™ manufactured by Torii & Co., Ltd.), an adsorptive carbon preparation (Kremezin™ manufactured by Kureha Chemical Industry Co., Ltd.), a cholestyramine preparation (Questran™, manufactured by Bristol-Myers Squibb Co.) and a precipitated calcium carbonate preparation (manufactured by Emisu Yakuhin K. K.), are all in dosage forms of bulk powders, powder preparations or capsules containing powders. Namely, there has been reported no example of preparations of this type in the form of tablets so far.

When orally administered, phosphate-binding polymers adsorb phosphorus in foods followed by excretion into the feces to thereby inhibit the absorption of phosphorus via the digestive tracts, thus regulating the phosphorus concentration in the blood. These phosphate-binding polymers are taken in a relatively large single dose, i.e., from 1 to 2 g. Because of reacting with water and thus swelling rapidly, the phosphate-binding polymers can be hardly taken as such.

Patients with dialysis to whom the phosphate-binding polymers are to be administered as remedies for hyperphosphatemia are frequently under restriction in water intake. It is therefore required to develop phosphate-binding polymer preparations which can be taken with a small amount of water. One of the promising dosage forms is tablets which can be small-sized by compression, in particular, coated tablets which would not disintegrate in the mouth and can be smoothly ingested. When processed into tablets by compressing, however, a phosphate-binding polymer alone gives only a poor tablet hardness and thus cannot be processed as such into a tablet preparation. Due to the high hygroscopicity and swelling properties of the phosphate-binding polymer, it is also impossible to produce a phosphate-binding polymer preparation by the wet granulation method with the use of water or a binder solution containing alcohols, etc. followed by drying.

To overcome these problems, it has been required to develop a production process which comprises blending a powdery phosphate-binding polymer with powdery additives having excellent molding characteristics and compressing the obtained mixture. Such a preparation should be designed by taking into consideration changes in the disintegration properties and dispersibility accompanying the compression. Since a phosphate-binding polymer is to be taken in a relatively large single dose, special regard should be paid to give a preparation with a high content of the active component.

Although the present inventors attempted to produce phosphate-binding polymer preparations in the form of tablets by using various additives described in U.S. Pat. No. 5,496,545, they could not produce any favorable tablets which contain phosphate-binding polymer having a sufficient hardness, a rapid disintegrative dispersibility and an ability to bind to phosphate.

DISCLOSURE OF THE INVENTION

Under these circumstances, the present inventors have conducted intensive studies to solve the above-mentioned problems. As a result, they have successfully found that a phosphate-binding polymer tablet which contains a large amount of the phosphate-binding polymer, has a sufficient hardness and shows rapid disintegrative dispersibility and an ability to bind to phosphate can be obtained by adding specific additives to a phosphate-binding polymer which has certain characteristics, thus completing the present invention. More particularly speaking, they have found that a tablet, which contains a phosphate-binding polymer having an average particle size of 400 μm or less, preferably 250 μm or less, containing particles of 500 μm or less, preferably 300 μm or less, in size at a ratio of 90% or more and having a moisture content of 1 to 14%, together with crystalline cellulose and/or low substituted hydroxypropylcellulose, has excellent characteristics.

MODE FOR CARRYING OUT THE INVENTION

Figure 1:
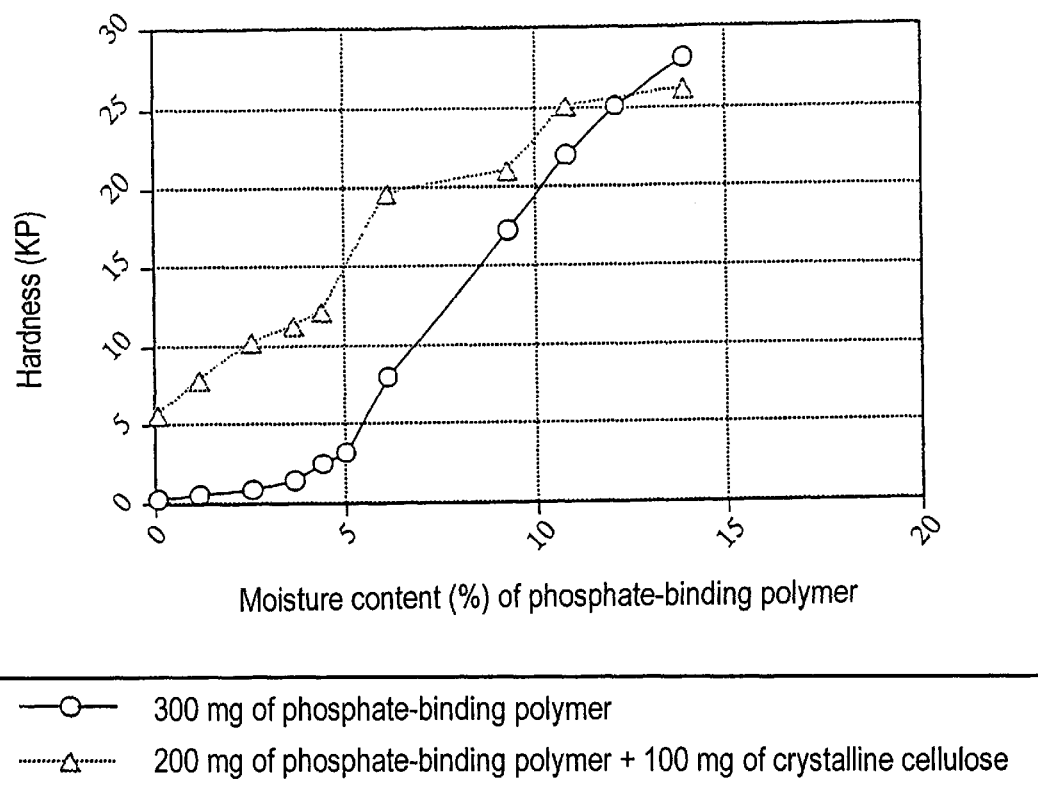
FIG. 1 provides a graph which shows a relationship between the moisture content of the phosphate-binding polymer and the tablet hardness in Example 2.

As the phosphate-binding polymer to be employed in the present invention, use can be made of, for example, one prepared by grinding the dry phosphate-binding polymer obtained by the method disclosed in U.S. Pat. No. 5,496,545 so as to give a ground material having an average particle size of 400 μm or less, preferably 250 μm or less, and containing particles of 500 μm or less, preferably 300 μm or less, in size at a ratio of 90% or more, and then further regulating the moisture content thereof to 1 to 14%. Among phosphate-binding polymers, a crosslinked polymer obtained by treating polyallylamine with epichlorohydrin is particularly suitable in the present invention.

Such dry phosphate-binding polymers as disclosed in U.S. Pat. No. 5,496,545 are as follows:

In one aspect, the polymer is characterized by a repeating unit having the formula

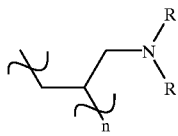
(1)

or a copolymer thereof, wherein n is an integer and each R, independently, is H or a lower alkyl (e.g., having between 1 and 5 carbon atoms, inclusive), alkylamino (e.g. having between 1 and 5 carbons atoms, inclusive, such as ethylamino) or aryl (e.g. phenyl) group.

In a second aspect, the polymer is characterized by a repeating unit having the formula

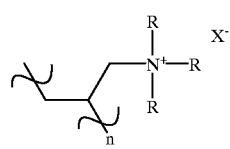
(2)

or a copolymer thereof, wherein n is an integer, each R, independently, is H or a lower alkyl (e.g. having between 1 and 5 carbon atoms, inclusive), alkylamino (e.g. having between 1 and 5 carbons atoms, inclusive, such as ethylamino) or aryl (e.g. phenyl) group, and each X⁻ is an exchangable negatively charged counterion.

One example of a copolymer according to the second aspect of the invention is characterized by a first repeating unit having the formula

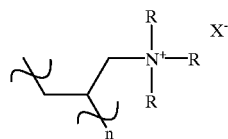
(2)

wherein n is an integer, each R, independently, is H or a lower alkyl (e.g. having between 1 and 5 carbon atoms, inclusive), alkylamino (e.g. having between 1 and 5 carbon atoms, inclusive, such as ethylamino) or aryl group (e.g. phenyl), and each X⁻ is an exchangeable negatively charged counterion; and further characterized by a second repeating unit having the formula

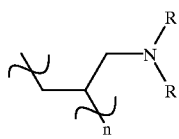
(3)

wherein each n, independently, is an integer and each R, independently, is H or a lower alkyl (e.g. having between 1 and 5 carbon atoms, inclusive), alkylamino (e.g. having between 1 and 5 carbons atoms, inclusive, such as ethylamino) or aryl group (e.g. phenyl).

In a fourth aspect, the polymer is characterized by a repeating unit having the formula

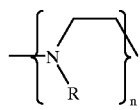
(4)

or a copolymer thereof, wherein n is an integer, and R is H or a lower alkyl (e.g. having between 1 and 5 carbon atoms, inclusive), alkylamino (e.g. having between 1 and 5 carbons atoms, inclusive, such as ethylamino) or aryl group (e.g. phenyl).

One example of a copolymer according to the second aspect of the invention is characterized by a first repeating unit having the formula

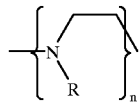
(4)

wherein n, is an integer and R is H or a lower alkyl (e.g. having between 1 and 5 carbon atoms, inclusive), alkylamino (e.g. having between 1 and 5 carbons atoms, inclusive, such as ethylamino) or aryl group (e.g. phenyl); and further characterized by a second repeating unit having the formula (5)

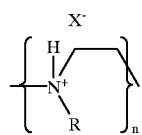

wherein each n, independently, is an integer and R is H or a lower alkyl (e.g. having between 1 and 5 carbon atoms, inclusive), alkylamino (e.g. having between 1 and 5 carbons atoms, inclusive, such as ethylamino) or aryl group (e.g. phenyl).

In a fifth aspect, the polymer is characterized by a repeating group having the formula (6)

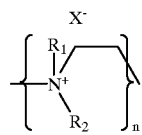

or a copolymer thereof, wherein n is an integer, and each $R_1$ and $R_2$, independently, is H or a lower alkyl (e.g. having between 1 and 5 carbon atoms, inclusive), alkylamino (e.g. having between 1 and 5 carbon atoms, inclusive, such as ethylamino) or aryl group (e.g. phenyl), and each $X^-$ is an exchangeable negatively charged counterion.

In one preferred polymer according to the fifth aspect of the invention, at least one of the R groups is a hydrogen group.

In a sixth aspect, the polymer is characterized by a repeat unit having the formula (7)

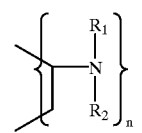

or a copolymer thereof, wherein n is an integer, and each $R_1$ and $R_2$, independently, is H, an alkyl group containing 1 to 20 carbon atoms, an alkylamino group (e.g. having between 1 and 5 carbon atoms, inclusive, such as ethylamino) or an aryl group containing 1 to 12 atoms (e.g. phenyl).

In a seventh aspect, the polymer is characterized by a repeat unit having the formula (8)

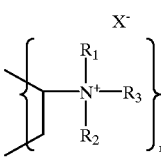

or a copolymer thereof, wherein n is an integer, and each $R_1$, $R_2$ and $R_3$, independently, is H, an alkyl group containing 1 to 20 carbon atoms, an alkylamino group (e.g. having between 1 and 5 carbon atoms, inclusive, such as ethylamino) or an aryl group containing 1 to 12 atoms (e.g. phenyl), and each $X^-$ is an exchangeable negatively charged counterion.

It is not preferable that the average particle size of the phosphate-binding polymer exceeds 400 μm since a sufficient hardness to give tablets can be hardly achieved in this case. When the moisture content of the phosphate-binding polymer is less than 1%, it is also impossible to obtain a sufficient hardness to give tablets and thus the tablet surface is liable to be abraded. When the moisture content thereof exceeds 14%, on the other hand, a sufficient hardness can be achieved. In this case, however, the resultant tablets undergo plastic deformation, which makes them inadequate as a medicinal preparation. To obtain tablets with improved administration properties, it is necessary to impart such surface strength to the tablets as to give a hardness of 6 KP or more (measured with a tablet hardness tester) and a weight loss of 1% or less in an friability test (100 revolutions). Moreover, the tablets should not undergo plastic deformation. To satisfy these requirements, it is required that the moisture content of the polymer falls within a range of 1 to 14%. The expression "a moisture content of 1 to 14%" as used herein means that after drying at 105° C. for 16 hours, the weight is reduced by 1 to 14%. It is preferable that the drying weight loss ranges from 2 to 14%. When the phosphate-binding polymer per se absorbs moisture in the course of grinding to give a moisture content of 1 to 14%, the phosphate-binding polymer may be used in the tablets of the present invention as such without regulating the moisture content any more.

The phosphate-binding polymer may be ground with an arbitrary apparatus without restriction, so long as a particle size of 500 μm or less and the average particle size as defined above can be achieved thereby. For example, use may be made of an impact grinder therefor.

The moisture content may be regulated by using a moisture-controlling agent, for example, a saturated aqueous solution of sodium chloride (25° C., relative humidity 75.3%), a saturated aqueous solution of calcium chloride (25° C., relative humidity 84.3%), a saturated aqueous solution of magnesium nitrate (25° C., relative humidity 52.8%), etc. or allowing the polymer to spontaneously absorb the moisture in the atmosphere. It is also possible to prepare the phosphate-binding polymer in such a manner as to give a moisture content within the range of 1 to 14% to thereby provide the polymer with the desired moisture content.

Although the crystalline cellulose to be used in the present invention is not particularly restricted, use may be made therefor of one showing a weight loss of 7% or less after drying at 105° C. for 3 hours. It is preferable to use marketed products, for example, Avicel™ PH101, PH102, PH301, PH302, etc. (manufactured by Asahi Chemical Industry Co., Ltd.) either alone or as a mixture thereof.

The low substituted hydroxypropylcellulose to be used in the present invention means one having a degree of substitution by hydroxypropoxyl group (—OC$_3$H$_6$OH) of 5.0 to 16.0% by weight. As a low substituted hydroxypropylcellulose, it is preferable to use marketed products such as LH-11, LH-21, LH-31, etc. (manufactured by Shin-Etsu Chemical Co., Ltd.) either alone or as a mixture thereof.

The amounts of the crystalline cellulose and/or the low substituted hydroxypropylcellulose to be used in the phosphate-binding polymer tablet according to the present invention may be arbitrarily determined by taking the dose of the phosphate-binding polymer as an oral preparation and the administration properties of the preparation into consideration. In a preferable embodiment, for example, the crystalline cellulose and/or the low substituted hydroxypropylcellulose are used in an amount of 10% by weight or more, preferably 30% by weight or more, based on the phosphate-binding polymer which has an average particle size of 250 μm or less, contains particles of 300 μm or less in size at a ratio of 90% or more and has a moisture content of 1 to 14%. When both of the crystalline cellulose and the low substituted hydroxypropylcellulose are added, it is preferable that the sum of the contents of these components is 10% by weight or more, preferably 30% by weight or more. From the viewpoint of the administration properties, etc. of the preparation, the upper limit of the content of the crystalline cellulose and/or the low substituted hydroxypropylcellulose is from 50 to 200% by weight.

Since the phosphate-binding polymer and the crystalline cellulose or the low substituted hydroxypropylcellulose have highly frictional natures, it is recommended to use a hydrogenated oil in the step of the continuous tabletting so as to relieve the load due to the rubbing between the blend and the punch of a tabletting machine. As the hydrogenated oil, use may be made of a marketed product such as Lubriwax™ manufactured by Freund Industrial Co., Ltd.

The phosphate-binding polymer tablet according to the present invention can be produced by blending the phosphate-binding polymer with the crystalline cellulose and/or low substituted hydroxypropylcellulose together with fillers (lactose, sucrose, mannitol, etc.), lubricants (magnesium stearate, polyethylene glycol, etc.), other additives conventionally employed in the art, perfumes, coloring agents, etc. followed by tabletting.

The phosphate-binding polymer tablet according to the present invention may be further processed into a film-coated tablet by coating the surface thereof with a film. In the film-coating, use may be made of water-soluble film bases such as hydroxypropylmethylcellulose and acrylic copolymers. It is particularly preferable to use hydroxypropylmethylcellulose therefor.

To further illustrate the present invention in greater detail, the following Examples and Referential Example will be given. However, it is to be understood that the present invention is not restricted thereto.

REFERENTIAL EXAMPLE

Epichlorohydrin was added as a crosslinking agent to polyallylamine and crosslinking polymerization was carried out to give a cationic phosphate-binding polymer wherein the primary amine (81.2% by mol) and the secondary amine (18.1% by mol) formed hydrochlorides at a ratio of about 40%. The obtained polymer was vacuum-dried to give a dry powder. This dry powder of the phosphate-binding polymer was ground by using a Fitz Mill (Model M5A manufactured by Fitzpatrick) and thus a moisture-containing phosphate-binding polymer (moisture content: 3.6%, ratio of particles of 300 μm or less in size: 99.7%) was obtained.

EXAMPLE 1

To 150 mg of the moisture-containing phosphate-binding polymer obtained in the above Referential Example, either crystalline cellulose (Avicel™ PH101 manufactured by Asahi Chemical Industry Co., Ltd.) or low substituted hydroxypropylcellulose (L-HPC LH31 manufactured by Shin-Etsu Chemical Co., Ltd.) was added in an amount of 150 mg, i.e., 100% by weight based on the weight of the phosphate-binding polymer. The obtained mixture was compressed under a static pressure (500 kg, 1,000 kg or 1500 kg) to give a tablet (diameter: 10 mm) weighing 300 mg. For comparison, 150 mg of the moisture-containing phosphate-binding polymer was blended 150 mg of one additive selected from among lactose (200M DMV), mannitol (manufactured by Kyowa Hakko Kogyo Co., Ltd.), methylcellulose (Metolose™ SM-15 manufactured by Shin-Etsu Chemical Co., Ltd.), talc (manufactured by Kihara Kasei), hydroxypropylcellulose (HPC-L manufactured by Nippon Soda Co., Ltd.), hydroxypropylmethylcellulose 2910 (HPMC TC- 5-RW manufactured by Shin-Etsu Chemical Co., Ltd.), carmellose calcium (ECG-505™ manufactured by Gotoku Yakuhin). The obtained mixture was compressed under a static pressure (500 kg, 1,000 kg or 1500 kg) to give a tablet (diameter: 10 mm) weighing 300 mg. Further, 300 mg of the moisture-containing phosphate-binding polymer was compressed under a static pressure to give a control tablet.

The hardness of each tablet thus obtained was measured with a hardness tester (Pharmatest). Also, tablets showing a hardness of 6 KP or more at a compression pressure of 1,000 kg were tested by using a disintegration tester (manufactured by Toyama Sangyo) with the use of water as a test fluid. Table 1 summarizes the results.

TABLE 1

| Additive | Tablet hardness (KP) (compression pressure: kg) | | | Disintegration |
|---|---|---|---|---|
| | 500 | 1000 | 1500 | 1000 kg (min) |
| crystalline cellulose | 9.4 | 17.7 | 24.1 | 0.5 |
| L-HPC | 5.4 | 11.4 | 17.1 | 10.5 |
| lactose | 0.7 | 1.8 | 3.3 | |
| mannitol | 0.4 | 1.2 | 2.0 | |
| methylcellulose | 10.2 | 20.0 | 24.4 | 22.3 |
| talc | 0.2 | 0.4 | 0.6 | |
| HPC-L | 13.3 | 22.6 | 25.1 | >30 |
| HPMC | 4.8 | 10.1 | 13.9 | >30 |
| ECG-505 | 1.3 | 5.0 | 9.2 | |
| (control) | 0.5 | 1.5 | 3.3 | |

As Table 1 shows, the tablets showing hardness exceeding 6 KP and disintegration time not longer than 15 minutes could be obtained by using crystalline cellulose or low substituted hydroxypropylcellulose (L-HPC).

EXAMPLE 2

The moisture-containing phosphate-binding polymer obtained in the above Referential Example was dried at 105° C. for 16 hours to give a dry phosphate-binding polymer powder (moisture content: less than 0.1%). In a desiccator, this dry powder was allowed to absorb moisture with the use of a saturated aqueous solution of sodium chloride as a moisture-controlling agent so as to prepare phosphate-binding polymers with moisture contents of 1.1 to 16.4%.

200 mg of each of these phosphate-binding polymers differing in moisture content was blended with 100 mg of crystalline cellulose (50% by weight based on the phosphate-binding polymer) and the resultant mixture was compressed under a static pressure of 1,000 kg to give a tablet (diameter: 10 mm) weighing 300 mg.

For comparison, 300 mg of each these phosphate-binding polymers differing in moisture content was compressed under a static pressure of 1,000 kg to give a tablet (diameter: 10 mm) weighing 300 mg.

The hardness of each tablet thus obtained was measured with a hardness tester. FIG. 1 shows the results. Moreover, tablets showing hardness of about 6 KP were each subjected to a friability test by revolving 100 times with the use of a friability tester (25 rpm, 4 minutes) and then the weight loss was determined. Table 2 summarizes the results.

TABLE 2

| Tablet composition | Moisture content in phosphate-binding polymer | Tablet hardness (KP) | Friability (wt. loss: %) |
|---|---|---|---|
| phosphate-binding polymer 300 mg | 6.1% | 8.0 | 3.6 |
| phosphate-binding polymer 200 mg crystalline cellulose 100 mg | 1.1% | 7.9 | 0.7 |
| phosphate-binding polymer 200 mg crystalline cellulose 100 mg | <0.1% | 5.6 | 1.6 |

Figure 2:
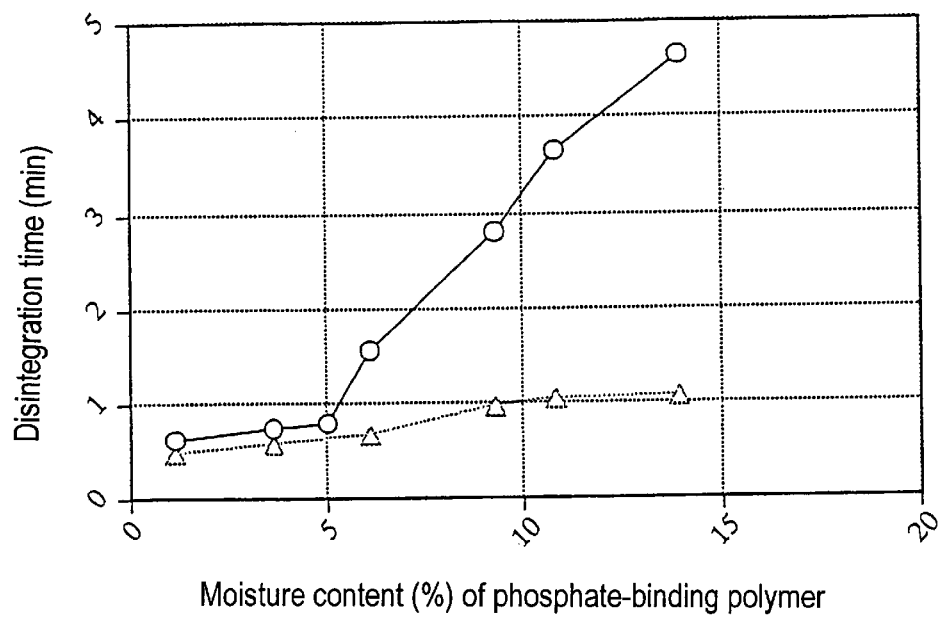
FIG. 2 provides a graph which shows a relationship between the average particle size of the phosphate-binding polymer and the disintegration time of the tablet in Example 2.

As FIGS. 1 and 2, and Table 2 show, the tablet produced by comprising the phosphate-binding polymer alone could not achieve sufficient hardness (6 KP or more) at a moisture content of 5% or less. Although the tablet with a moisture content of 6.1% showed a hardness of 8 KP, the friability exceeded the allowable level (weight loss: 1% or less) specified in United States Pharmacopoeia. That is to say, it had a poor surface strength. In the tablets produced by compressing the phosphate-binding polymer containing 9% or more moisture alone, the disintegration time was prolonged with an increase in the tablet hardness. The tablets with moisture content of 16% or more suffered from plastic deformation, thus showing inadequate tablet properties. When the phosphate-binding polymer was blended with crystalline cellulose, in contrast thereto, a sufficient hardness and tablet surface strength were observed and rapid disintegration (disintegration time: about 1 minute) was achieved within a moisture content range of 1 to 14%.

EXAMPLE 3

The moisture-containing phosphate-binding polymer obtained in the above Referential Example was sieved by using a sonic shifter (manufactured by Seishin Kigyo) through 60 mesh (250 $\mu$m), 80 mesh (180 $\mu$m), 150 mesh (106 $\mu$m) and 270 mesh (53 $\mu$m) sieves to give a phosphate-binding polymer of 250 $\mu$m or more in average particle size, one of from 180 to 250 $\mu$m in average particle size, one of from 106 to 180 $\mu$m in average particle size, one of from 53 to 106 $\mu$m in average particle size and one of 53 $\mu$m or less in average particle size.

To 200 mg of each of these phosphate-binding polymers differing in average particle size, 100 mg of crystalline cellulose (50% by weight based on the weight of the phosphate-binding polymer) was added and the obtained mixture was compressed under a static pressure of 1,000 kg to give a tablet (diameter: 10 mm) weighing 300 mg.

For comparison, 300 mg of each of the phosphate-binding polymers differing in average particle size was compressed alone under a static pressure of 1,000 kg to give a tablet (diameter: 10 mm) weighing 300 mg.

Figure 3:
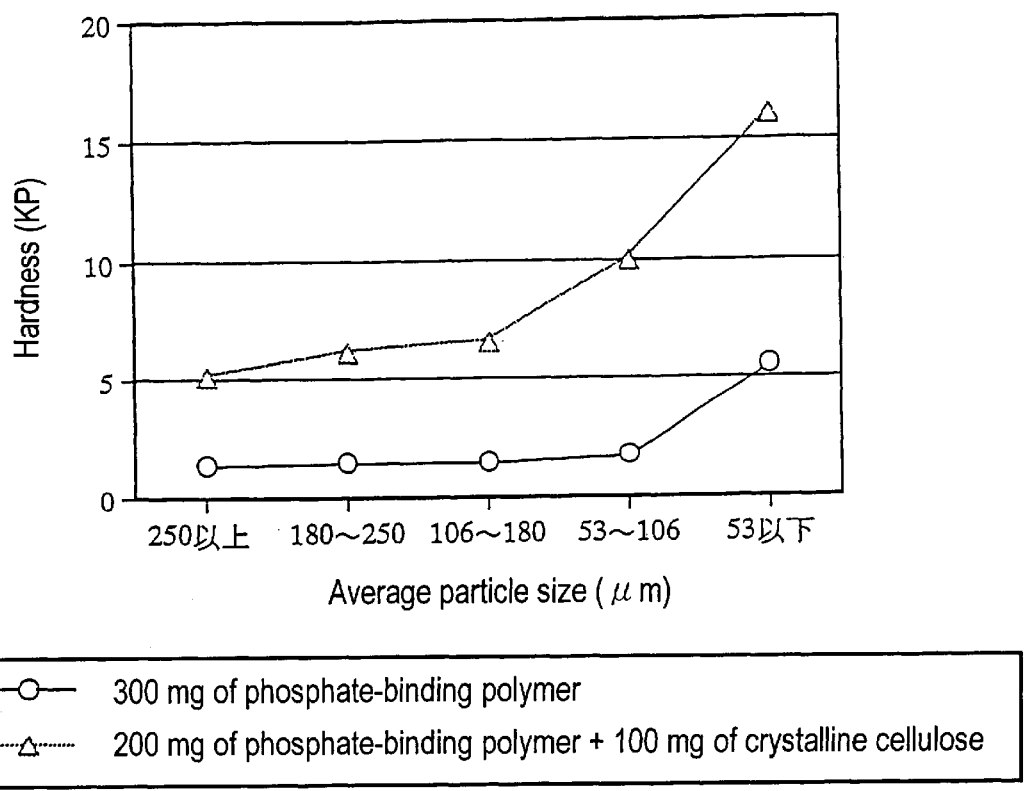
FIG. 3 provides a graph which shows a relationship between the average particle size of the phosphate-binding polymer and the tablet hardness in Example 3.
Figure 4:
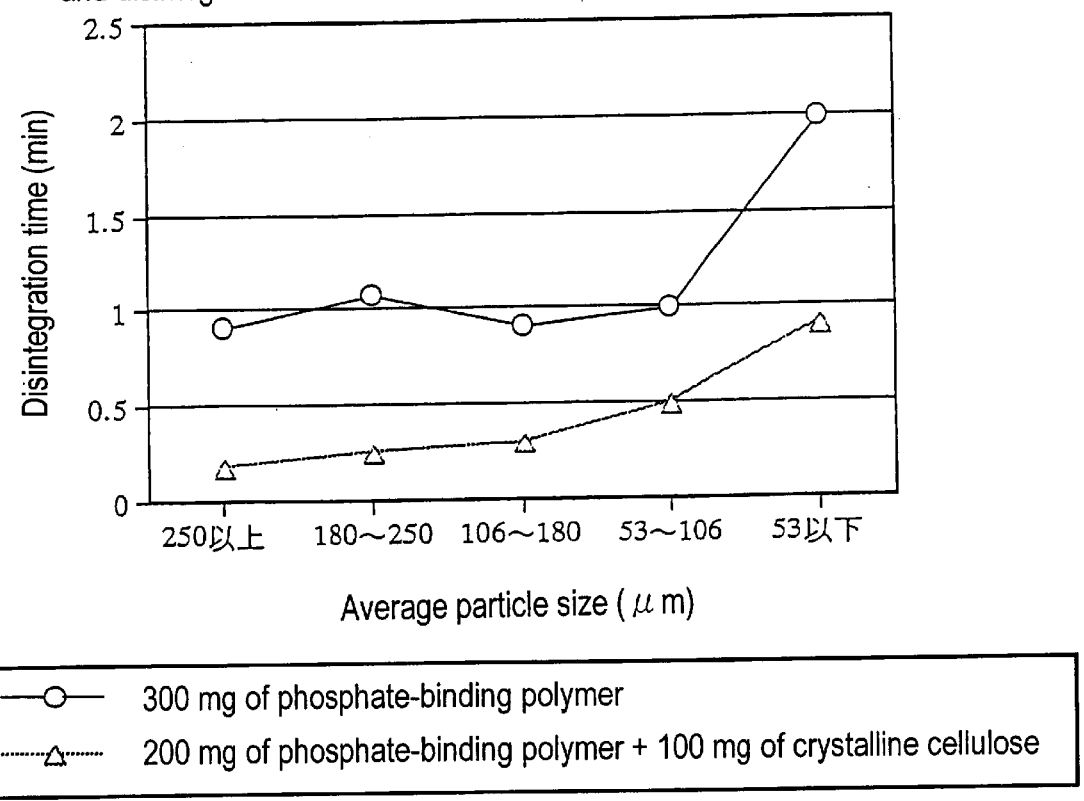
FIG. 4 provides a graph which shows a relationship between the average particle size of the phosphate-binding polymer and the disintegration time of the tablet in Example 3.

FIG. 3 shows the results of the measurement of the hardness of each tablet thus obtained with a hardness tester, while FIG. 4 shows the results of the determination of the disintegration time thereof (test fluid: water).

As FIGS. 3 and 4 show, none of the tablets produced by compressing the phosphate-binding polymers alone could achieve a sufficient hardness (6 KP or more). When crystalline cellulose was added to the phosphate-binding polymers, in contrast thereto, the hardness was elevated with a decrease in the average particle size. A sufficient hardness and rapid disintegration were established at an average particle size of 250 $\mu$m or less.

EXAMPLE 4

200 g of the moisture-containing phosphate-binding polymer obtained in the above Referential Example was blended with 97.6 g of crystalline cellulose and 2.4 g of magnesium stearate (manufactured by Nitto Kasei) employed as a lubricant. The obtained mixture was compressed by using a rotary tabletting machine (Model HT-P18A manufactured by Hata Iron Worker) under a pressure of 2,000 kg to give tablets (uncoated) of 9.5 mm in diameter each weighing 300 mg and containing 200 mg of the phosphate-binding polymer.

When measured with a hardness tester (a contester), these tablets showed a tablet hardness of 7.7 KP.

Further, the uncoated tablet containing 200 mg of the phosphate-binding polymer was coated with a film comprising 8.25 mg of hydroxypropylmethylcellulose 2910 (HPMC TC-5-MW manufactured by Shin-Etsu Chemical Co., Ltd.), 1.26 mg of polyethylene glycol 6000 (manufactured by Nippon Oil and Fats Co., Ltd.), 1.8 mg of titanium oxide (A-100 manufactured by Ishihara Sangyo Co., Ltd.) and 0.69 mg of talc by using a coating machine (Dria Coater Model DRC-500 manufactured by Powrex Corporation) to give a film-coated tablet preparation.

Figure 5:
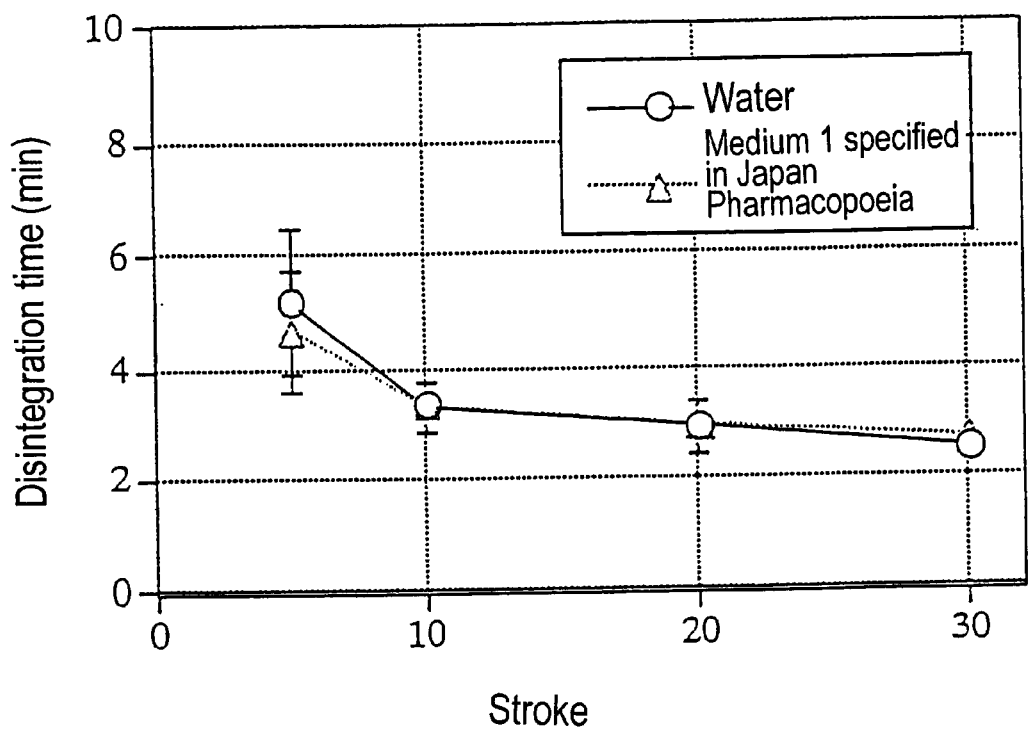
FIG. 5 provides a graph which shows the disintegration properties (i.e., a relationship between the strokes of the disintegration tester and the disintegration time) of the phosphate-binding polymer preparation in Example 4.

The film-coated tablets thus obtained were tested by using a disintegration tester at 5 to 30 strokes per minute with the use of two test fluids (pH 1.2: official liquid 1, specified in "Japanese Pharmacopoeia", water). FIG. 5 shows the results.

As FIG. 5 shows, the phosphate-binding polymer preparation containing crystalline cellulose was rapidly disintegrated within the acidic to neutral region while scarcely affected by the stirring strength (stroke).

EXAMPLE 5

Figure 6:
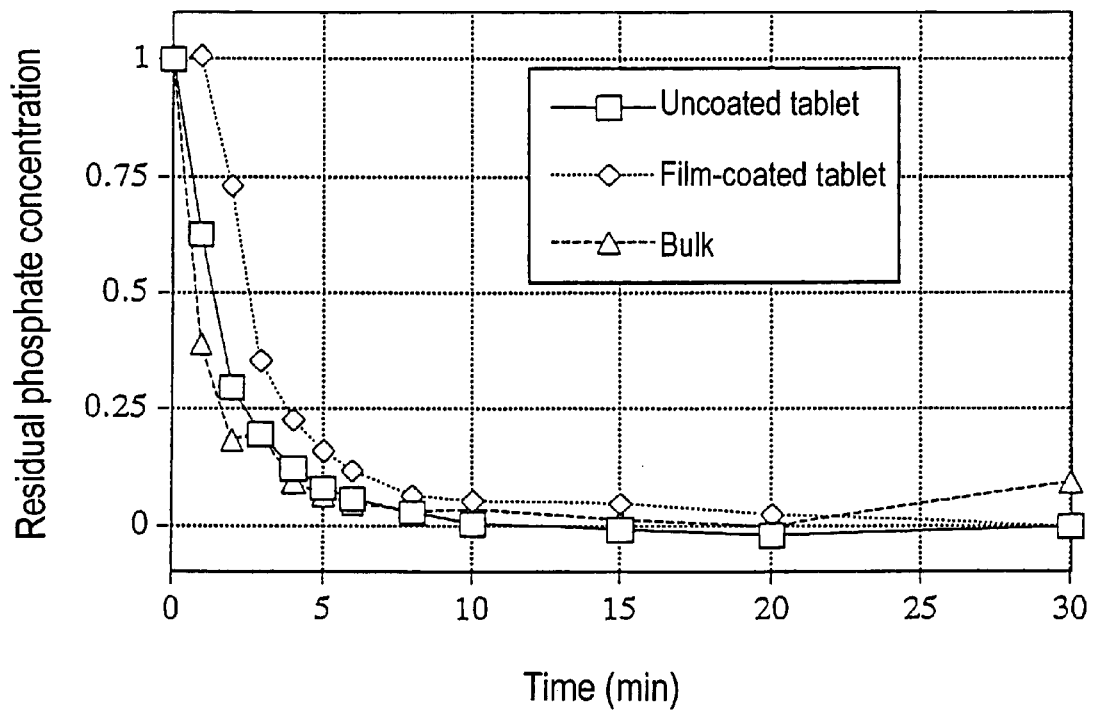
FIG. 6 provides a graph which shows the phosphate-binding profile of the phosphate-binding polymer preparation in Example 5.

To evaluate the drug effects, 5 uncoated tablets and 5 film-coated tablets, each containing 200 mg of the phosphate-binding polymer, prepared in Example 4 were examined in the ability to bind to phosphate in 200 ml of a test fluid which had been prepared by dissolving 4.7 g of sodium chloride, 21.3 g of N,N-bis(2-hdyroxyethyl)-2-aminoethanesulfonic acid and 0.544 g of potassium dihydrogenphosphate in water, regulating the pH value to 7 and heating to 37° C., while rotating puddles at 100 rpm. The ability to bind to phosphate was evaluated by monitoring the residual phosphate concentration in the test fluid with the passage of time throughout the process of the disintegration of the tablets, dispersion of the phosphate-binding polymer and adsorption of phosphate. The initial phosphate concentration in the test fluid and the one at the completion of the adsorption are referred to respectively as 1 and 0. FIG. 6 shows the results.

As FIG. 6 shows, the phosphate-binding polymer preparations containing crystalline cellulose were able to rapidly bind to phosphate.

Industrial Applicatibility

The phosphate-binding polymer tablet according to the present invention contains the active component at a high ratio, has excellent ability to bind to phosphate and undergoes rapid disintegration within an acidic to neutral region while scarcely affected by the stirring strength. Accordingly, it is an excellent preparation capable of regulating changes in bioavailability due to the gastrointestinal motions and ph value.

What is claimed is:

1. A tablet comprising a phosphate-binding polymer which has an average particle size of 400 μm or less, contains particle size of 500 μm or less in size at a ratio of 90% or more, and has a moisture content of 1 to 14%, together with crystalline cellulose and/or low substituted hydroxypropylcellulose, said phosphate-binding polymer being a polymer selected from a group consisting of (a) a polymer with a repeating unit having the formula

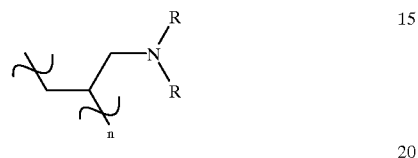

or a copolymer thereof, wherein n is an integer and each R, independently, is H or a lower alkyl, alkylamino, or aryl group;

(b) a polymer with a repeating unit having the formula

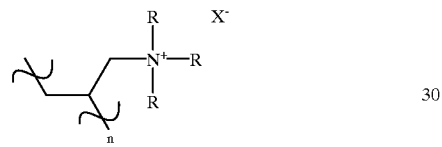

or a copolymer thereof, wherein n is an integer and each R, independently, is H or a lower alkyl, alkylamino or aryl group, and each X is an exchangeable negatively charged counterion selected from the group consisting of organic ions, inorganic ions or combinations thereof;

(c) a copolymer according to (b) with a first repeating unit having the formula

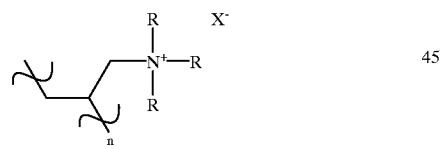

wherein n is an integer, each R, independently, is H or a lower alkyl, alkylamino, or aryl group, and each X is an exchangeable negatively charged counterion selected from the group consisting of organic ions, inorganic ions or combinations thereof, and a second repeating unit having the formula

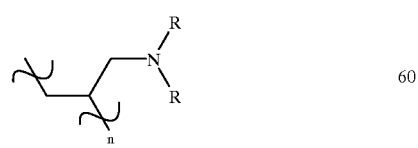

wherein each n, independently, is an integer and each R, independently, is H or a lower alkyl, alkylamino, or aryl group;

(d) a polymer with a repeating unit having the formula

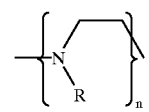

or a copolymer thereof, wherein n is an integer and R is H or a lower alkyl group, alkylamino, or aryl group;

(e) a copolymer according to (b) with a first repeating unit having the formula:

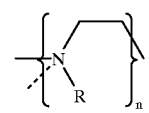

wherein n is an integer, and R is H or a lower alkyl, alkylamino, or aryl group, and a second repeating unit having the formula

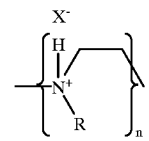

wherein each n, independently, is an integer, and R is H or a lower alkyl, alkyamino, or aryl group;

(f) a polymer with a repeating unit having the formula

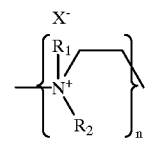

or a copolymer thereof, wherein n is an integer, and each $R_1$ or $R_2$, independently, is H or a lower alkyl, alkylamino, or aryl group, and each X is an exchangeable negatively charged counterion selected from the group consisting of organic ions, inorganic ions or combinations thereof;

(g) a polymer characterized by a repeating unit having the formula

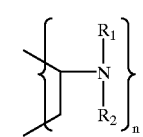

or a copolymer thereof, wherein n is an integer each $R_1$ or $R_2$, independently, is H, an alkyl group containing 1 to 20 carbon atoms, an alkyamino group having between 1 and 5 carbon atoms, inclusive), or an aryl group containing 1 to 12 atoms and (h) a polymer with a repeating unit having the formula

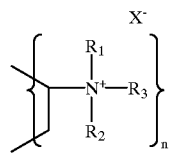

or a copolymer thereof, wherein n is an integer and each $R_1$ and $R_3$ independently, is H, an alkyl group containing 1 to 20 carbon atoms, an alkylamino group or an aryl group containing 1 to 12 atoms, and each X is an exchangeable negatively charged counterion selected from the group consisting of organic ions, inorganic ions or combinations thereof.

2. A tablet comprising a phosphate-binding polymer which has an average particle size of 400 μm or less, contains particle size of 500 μm or less in size at a ratio of 90% or more, and has a moisture content of 1 to 14%, together with crystalline cellulose and/or low substituted hydroxylpropylcellulose, said phosphate-binding polymer being a polymer obtained by treating polyallylamine with epichlorohydrin so as to crosslink the same.

3. The tablet as claimed in claim 1, wherein said phosphate-binding polymer has an average particle size of 250 μm or less and contains particles of 300 μm or less in size at a ratio of 90% or more.

4. The tablet as claimed in claim 1, wherein the content of crystalline cellulose and/or low substituted hydroxypropylcellulose is 10% by weight or more based on the weight of said phosphate-binding polymer.

5. The tablet as claimed in claim 1, wherein said low substituted hydroxypropylcellulose has a degree of hydroxypropoxyl-substitution of from 5.0 to 16.0% by weight.

6. The tablet as claimed in claim 1, which further contain a hydrogenated oil.

7. The tablet as claimed in claims 1, which is further surface-coated with a water-soluble film base.

8. A process for producing phosphate-binding polymer tablet which comprises grinding polyallylamine or a phosphate-binding polymer obtained by crosslinking the same so as to give a ground material having an average particle size of 400 μm or less and containing particle of 500 μm or less in size at a ratio of 90% or more, regulating the moisture content thereof to 1 to 14%, blending the ground material with crystalline cellulose and/or low substituted hydroxypropylcellulose, and then tabletting the resultant mixture.

9. The process as claimed in claim 8, wherein said phosphate-binding polymer is ground so as to give ground material having an average particle size of 250 μm or less and containing particles of 300 μm or less in size at a ratio of 90% or more.

10. The tablet as claimed in claim 3, wherein the content of crystalline cellulose and/or low substituted hydroxypropylcellulose is 10% by weight or more based on the weight of said phosphate-binding polymer.

11. The tablet as claimed in claim 3, wherein said low substituted hydroxypropylcellulose has a degree of hydroxypropoxyl-substitution of from 5.0 to 16% by weight.

12. The tablet as claimed in claim 11, which further contains a hydrogenated oil.

13. The tablet as claimed in claim 12, which is further surface-coated with a water-soluble film base.

14. The tablet as claimed in claim 2, wherein said phosphate-binding polymer has an average particle size of 250 μm or less and contains particles of 300 μm or less in size at a ratio of 90% or more.

15. The tablet as claimed in claim 2, wherein the content of crystalline cellulose and/or low substituted hydroxypropylcellulose is 10% by weight or more based on the weight of said phosphate-binding polymer.

16. The tablet as claimed in claim 2, wherein said low substituted hydroxypropylcellulose has a degree of hydroxypropoxyl-substitution of from 5.0 to 16.0% by weight.

17. The tablet as claimed in claim 2, which further contain a hydrogenated oil.

18. The tablet as claimed in claims 2, which is further surface-coated with a water-soluble film base.

19. The tablet as claimed in claim 14, wherein said low substituted hydroxypropylcellulose has a degree of hydroxypropoxyl-substitution of from 5.0 to 16% by weight.

20. The tablet as claimed in claim 19, which further contains a hydrogenated oil.

* * * * *